United States Patent [19]

Kato et al.

[11] Patent Number: 5,189,057
[45] Date of Patent: Feb. 23, 1993

[54] SACCHAROASCORBIC ACID DERIVATIVES

[75] Inventors: Koichi Kato, Kawanishi; Hirotomo Masuya; Moriya Norihiko, both of Kawabe, all of Japan.

[73] Assignee: Takeda Chemical Industries, Ltd., Osaka, Japan

[21] Appl. No.: 733,209

[22] Filed: Jul. 19, 1991

[30] Foreign Application Priority Data

Jul. 20, 1990 [JP] Japan .................. 2-193425
May 27, 1991 [JP] Japan .................. 3-121033

[51] Int. Cl.$^5$ .................. A01N 43/20; A01N 43/24; C07D 305/12; C07D 307/93
[52] U.S. Cl. .................. 514/473; 549/315; 549/316; 549/317
[58] Field of Search .................. 549/315, 316, 317; 514/473

[56] References Cited

U.S. PATENT DOCUMENTS 5,043,459  8/1991  Matsumura et al. .................. 549/313

FOREIGN PATENT DOCUMENTS 0202589  11/1986  European Pat. Off. .
0339486  11/1989  European Pat. Off. .
0381472  8/1990  European Pat. Off. .
0396312  11/1990  European Pat. Off. .
62-13  1/1987  Japan .
63-66160  3/1988  Japan .

OTHER PUBLICATIONS

Plough et al., Biochimica et Biophysicia Acta, vol. 24, pp. 278–282 (1957).
Rijken et al., The Journal of Biological Chemistry, vol. 256, No. 13, (Jul. 10, 1981), pp. 7035–7041.
Jukes, Trends in Biochemical Sciences, vol. 4, No. 1 (Jan. 1979).
Pannell et al., Blood, vol. 67, No. 5 (May 1986) pp. 1215–1223.
Tengborn, Fibrinolysis, vol. 1 (1987) pp. 24–32.

*Primary Examiner*—C. Warren Ivy
*Assistant Examiner*—Raymond Covington
*Attorney, Agent, or Firm*—Wenderoth, Lind & Ponack

[57] ABSTRACT

A compound of the formula (I):

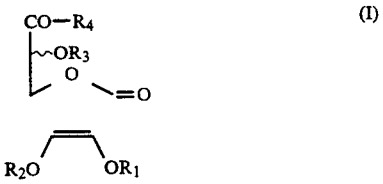

wherein $R_1$ and $R_2$ each is a hydrocarbon residue, $R_3$ is a sulfo group or phosphono group, —CO—$R_4$ is an esterified carboxyl group, a thiol-esterified carboxyl group or an amidated carboxyl group; and ~ represents the absolute configuration of R or S, or its salt, which is useful for preventing and treating thrombosis.

14 Claims, No Drawings

SACCHAROASCORBIC ACID DERIVATIVES

FIELD OF THE INVENTION

The present invention relates to a pharmaceutical composition for preventing and treating thrombosis which contains a saccharoascorbic acid derivative as an active component. More particularly, the present invention provides a pharmaceutical composition which can prevent and treat thrombosis by the action of the saccharoascorbic acid derivative on vascular endothelial cells to accelerate fibrinolysis reaction.

BACKGROUND OF THE INVENTION

Blood circulates in healthy blood vessels, while always maintaining fluidity. However, in morbid states such as inflammation, injury, vascular endothelial disorders and the like, blood coagulation is proceeded by a cascade reaction wherein various coagulation factors participate and, at the final stage thereof, conversion of fibrinogen into fibrin occurs to coagulate blood. A significant example thereof is intravascular coagulation, in particular, thrombosis is a representative typical example. Fibrin deposited in a blood vessel clogs up the vessel, which occasionally causes mortal diseases such as myocardial infarction, brain infarction and the like.

It is known that there is an enzyme precursor, called plasminogen, in circulating blood and that the precursor is converted into plasmin due to restrictive decomposition by a plasminogen activator. Plasmin, which is a serine protease having affinity to fibrin, decomposes and dissolves fibrin. The series of these reactions is called a fibrinolysis reaction. A drug, which can accelerate the fibrinolysis reaction, dissolves and removes fibrin once formed, thereby effective for treatment of thrombosis and prevention of a recurrence thereof.

Hitherto, plasminogen activator preparations or protein preparations such as urokinase, tissue plasminogen activator, streptokinase, prourokinase and the like have been used as drugs which accelerate the fibrinolysis reaction by activating the enzyme precursor, plasminogen, to form plasmin [Biochim. Biophys. Acta, 24, 24 (1957); J. Biol. Chem., 256, 7035 (1981); Trends. Biochem. Sci., 4, 1 (1979); and Blood, 67, 1215 (1986)].

A pharmaceutical composition for preventing and treating thrombosis comprising as an active component retinoyl L-ascorbate (Japanese Patent Laid-Open Publication No. 66160/1988) and comprising as active components retinoic acid and L-ascorbic acid (Japanese Patent Laid-Open Publication No. 13/1987) have also been known.

Further, it has been reported that steroids such as stanozolol and the like have antithrombotic activities [Fibrinolysis, Vol. 1, pp 29-32 (1987)].

However, these known drugs have various drawbacks. For example, the enzymatic preparations such as urokinase, tissue plasminogen activator and the like have a relatively short half life in blood, so that systemic hemorrhagic trend is caused by excess administration of said enzymatic preparations. Since streptokinase is a foreign protein derived from bacteria, it has immunogenicity. An ascorbic acid, retinoic acid and the like are required to have a high concentration for manifesting its activities. Further, steroids have strong side effects.

Thus, it is desired to develop a new drug for treating and preventing thrombosis which has improved activities with minimized side effects.

SUMMARY OF THE INVENTION

The present inventors have aimed at the fact that plasminogen activator produced by vascular endothelial cells acts on plasminogen to produce plasmin, and have widely investigated substances which can promote and/or induce the production of plasminogen activator by vascular endothelial cells. As a result, the present inventors have succeeded in creating saccharoascorbic acid derivatives having a completely novel structure and, at the same time, found that these derivatives have these activities.

Thus, according to the present invention, there is provided a pharmaceutical composition for preventing and treating thrombosis which comprises a compound of the formula (I):

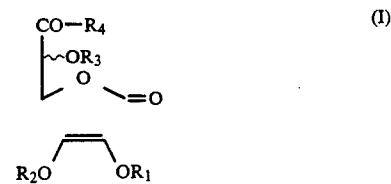

wherein $R_1$ and $R_2$ each is a hydrocarbon residue, $R_3$ is a sulfo group or phosphono group, $-CO-R_4$ is an esterified carboxyl group, a thiol-esterified carboxyl group or an amidated carboxyl group; and ~ represents the absolute configuration of R or S, or a pharmaceutically acceptable salt thereof.

DETAILED DESCRIPTION OF THE INVENTION

The term "thrombosis" used herein means all morbidities accompanying intravascular coagulation of blood and all diseases caused by such a coagulation are included in the objective diseases of the present invention.

In the formula (I), when the hydroxy group at the 5 position is located at the right side (R-configuration), the compound is L-gulosaccharoascorbic acid. When the hydroxy group at the 5-position is located at the left side (S-configuration), the compound is D-glucosaccharoascorbic acid.

A hydrocarbon residue is a group formed by removing one hydrogen atom from a hydrocarbon. The hydrocarbon residue represented by $R_1$ and $R_2$ is ether-linked through an oxygen atom at the 2-position or 3-position of the compound (I). The hydrocarbon residue has generally 1 to 24 carbon atoms. Specifically, the hydrocarbon residue may be an alkyl group or an aralkyl group.

Examples of the alkyl groups are a straight, branched or cyclic alkyl group having 1 to 24 carbon atoms such as methyl, ethyl, propyl, i-propyl, butyl, i-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl, cyclopropyl, cyclohexyl, cycloheptyl, cyclooctyl or the like.

These groups may have substituents such as a halogen (fluorine, chlorine, bromine, iodine, etc.), carboxyl or its ester, carbamoyl, nitro, cyano, an alkoxy having 1 to 4 carbon atoms, or the like. The above-mentioned cycloalkyl group may have another substituent in addition to the above ones, i.e., a straight or branched alkyl group having 1 to 4 carbon atoms.

Examples of the aralkyl groups include a $C_{1-4}$ lower alkyl group substituted with an aromatic group such as phenyl. The total number of carbon atoms is preferably 7 to 24. Typical aralkyl group includes benzyl, phenethyl, furfuryl, phenylpropyl, phenylbutyl, etc., among which benzyl is preferable.

These aralkyl groups may have substituents on the aromatic group thereof. Examples of the substituents are a halogen such as fluorine, chlorine, bromine, iodine or the like, carboxyl or its ester, carbamoyl, phenyl, nitro, cyano, an $C_{1-4}$ alkoxy, an $C_{1-4}$ alkyl optionally substituted with a halogen or the like.

The esterified or thiol-esterified carboxyl group represented by $-CO-R_4$ is represented by $-CO-O-R_5$ and $-CO-S-R_6$ wherein $R_5$ and $R_6$ each represents a hydrocarbon residues having 1 to 24 carbon atoms. Examples of the hydrocarbon residues are the same as those mentioned above.

The amidated carboxyl group represented by $-CO-R_4$ is represented by

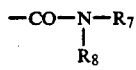

wherein $R_7$ and $R_8$ each is, the same or different, a hydrogen atom or a hydrocarbon residue having 1 to 24 carbon atoms, or $R_7$ and $R_8$ may combine to form $-(CH_2)_n-$ in which n is an integer of 4 to 7. When $R_7$ and $R_8$ form $-(CH_2)_n-$, the resultant ring may have substituent(s). Examples of the substituents are the same as those mentioned for $R_1$ and $R_2$. The specific examples of the hydrocarbon residues are the same as those mentioned above.

Examples of the hydrocarbon residues represented by $R_5$, $R_6$, $R_7$ and $R_8$ are a straight or branched alkyl, cycloalkyl, alkenyl, alkynyl, aralkyl, aryl or the like as described above. Examples of the alkyl, cycloalkyl and aralkyl groups are those as mentioned for $R_1$ and $R_2$. Used alkenyl and alkynyl groups are those having 2 to 24 carbon atoms.

These groups may have substituent(s) as mentioned for $R_1$ and $R_2$.

Examples of the alkenyl groups of 2 to 24 carbon atoms include vinyl, allyl, butenyl, pentenyl, hexenyl, heptenyl, octenyl, nonenyl, decenyl, undecenyl, dodecenyl, tridecenyl, tetradecenyl, pentadecenyl, heptadecenyl, octadecenyl, nonadecenyl, icosenyl, henicosenyl, docosenyl, tricosenyl, tetracosenyl, etc.

Examples of the alkynyl groups having 2 to 24 carbon atoms include ethynyl, propynyl, butynyl, pentynyl, hexynyl, heptynyl, octynyl, nonynyl, decynyl, undecynyl, dodecynyl, tridecynyl, tetradecynyl, pentadecynyl, heptadecynyl, octadecynyl, nonadecynyl, icosynyl, henicosynyl, tricosynyl, tetracosynyl, etc.

Examples of the aryl groups, e.g., having 4 to 24 carbon atoms include carbocyclic aromatic compounds and heterocyclic aromatic compounds such as phenyl, furyl, thienyl, pyridyl, naphthyl groups, etc.

Specific examples of the compounds represented by the formula (I) or the salts thereof are 2,3-di-O-benzyl-5-O-phosphono-D-glucosaccharoascorbic acid n-octadecylamide sodium salt, 2,3-di-O-benzyl-5-O-phosphono-D-glucosaccharoascorbic acid benzenethiolester sodium salt, 2,3-di-O-benzyl-5-O-phosphono-D-glucosaccharoascorbic acid N,N-pentamethyleneamide sodium salt, 2,3-di-O-benzyl-5-O-phosphono-D-glucosaccharoascorbic acid n-decylamide sodium salt, 2,3-di-O-benzyl-5-O-phosphono-D-glucosaccharoascorbic acid amide sodium salt, 2,3-di-O-benzyl-5-O-phosphono-D-glucosaccharoascorbic acid methylester sodium salt, 2,3-di-O-phosphono-D-glucosaccharoascorbic acid tert-butylester sodium salt, 2,3-di-O-benzyl-5-O-phosphono-glucosaccharoascorbic acid n-octadecylester sodium salt, 2,3-di-O-benzyl-5-O-sulfo-D-glucosaccharoascorbic acid n-octadecylamide sodium salt, 2,3-di-O-benzyl-5-O-sulfo-D-glucosaccharoascorbic acid benzenethiolester sodium salt, 2,3-di-O-benzyl-5-O-sulfo-D-glucosaccharoascorbic acid N,N-pentamethyleneamide sodium salt, 2,3-di-O-benzyl-5-O-sulfo-D-glucosaccharoascorbic acid n-decylamide sodium salt, 2,3-di-O-benzyl-5-O-sulfo-D-glucosaccharoascorbic acid amide sodium salt, 2,3-di-O-benzyl-5-O-sulfo-D-glucosaccharoascorbic acid methylester sodium salt, 2,3-di-O-benzyl-5-O-sulfo-D-glucosaccharoascorbic acid tert-butylester sodium salt, 2,3-di-O-benzyl-5-O-sulfo-D-glucosaccharoascorbic acid n-octadecylester sodium salt or the like.

Saccharoascorbic acid derivatives of the formula(I), in which $R_1$ and $R_2$ each is a benzyl group and $-CO-R_4$ is an esterified carboxyl group of $-CO-O-R_5$ can be produced by the process disclosed in Japanese Laid-Open Patent Publication No. 85970/1989 (EP-A-0 295 842).

The compounds of this invention can be also produced by using saccharoascorbic acid of the formula (II):

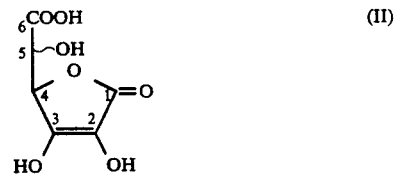

as the starting material.

In the formula (II), when the hydroxyl group at the 5-position is located at the right side (R-configuration), the compound is L-gulosaccharoascorbic acid which is a known compound (for example, U.S. Pat. No. 2,428,438). When the hydroxyl group at the 5-position is located at the left side (S-configuration), the compound is D-glucosaccharoascorbic acid and is prepared by treating 2-keto-D-glucaric acid (D-arabino-2-hexulosaric acid), or its 2,3-0-acetal or -ketal with an acid (Japanese Laid-Open Patent Publication No. 228091/1987).

That is, the compound having the thiol-esterified carboxyl group of $-CO-S-R_6$ can be prepared according to the scheme 1:

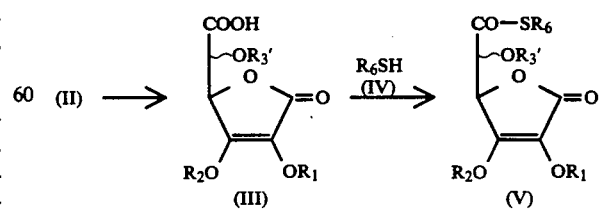

wherein $R_1$, $R_2$ and $R_6$ have the same meanings as defined above and $R_3'$ is a hydrogen atom or an acyl group.

As seen from the scheme 1, the compound (III) is reacted with a thiol of the formula (IV) to obtain the compound of the formula (V). Subsequently, the group of $R_1$, $R_2$ or $R_3'$ can be subjected to elimination reaction, if necessary. The starting compound (III) can be prepared from the saccharoascorbic acid compound (II) by a known method, e.g., the one disclosed in EP-A-0 295 842. The compounds other than the known compounds can be prepared by the methods as described in schemes 4 and 5 hereinafter.

The reaction of the compound (III) with the compound (IV) to produce the compound (V) can be carried out according to a known thiol ester synthesis. For example, it can be carried out using a carboxyl-activating reagent in an organic solvent. Examples of the carboxyl-activating reagents include N,N-dicyclohexylcarbodiimide, diethyl phosphorocyanidate, carbonyldiimidazole, 1-methyl-2-halopyridinium iodide and the like. Examples of the organic solvents include hydrocarbons such as hexane, benzene, toluene and the like, halogenated hydrocarbons such as chloroform, dichloromethane, 1,2-dichloroethane and the like, ethers such as diethyl ether, tetrahydrofuran, dioxane and the like, ethyl acetate, acetonitrile, dimethylformamide and the like.

The compound (III) may be converted into the corresponding acid halide using a halogenating agent such as phosphorus pentachloride, thionyl chloride, thionyl bromide or triphenylphosphine dibromide or the like. The reaction temperature for this thiol-esterification reaction ranges from $-10°$ C. to $120°$ C. The reaction time is about 1 to 5 hours.

When $R_1$ and/or $R_2$ in the compound (V) is a benzyl group optionally having substituent(s), e.g., benzyl, p-methyl benzyl, o-nitrobenzyl, p-nitrobenzyl, p-chlorobenzyl, p-bromobenzyl, p-cyanobenzyl, diphenylmethyl, etc., this benzyl group can be eliminated if necessary.

The elimination reaction can be carried out by using a Lewis acid such as aluminum chloride, titanium tetrachloride, stannic chloride, boron trifluoride ether complex, boron tribromide, zinc choloride or the like. Any reaction solvent can be used without particular limitation so long as it does not interfere with the reaction. Examples of the solvents are halogenated hydrocarbons such as chloroform, dichloromethane, 1,2-dichloroethane, or the like, ethers such as diethylether, tetrahydrofuran, dioxane or the like or acetonitrile. The reaction temperature ranges from $-10$ to $120°$ C. and the reaction time ranges from about 1 to 20 hours.

When $R_3'$ of the compound (V) is an acyl group, this acyl group can be eliminated if required. This elimination reaction can be carried out by using an acid or base.

Any acid or base can be used without particular limitation. Examples of the acid are hydrogen chloride, hydrogen bromide, hydrogen fluoride, sulfuric acid, fluorosulfuric acid, perchloric acid, phosphoric acid, boric acid, p-toluenesulfonic acid, trifluoromethanesulfonic acid, methanesulfonic acid, trifluoroacetic acid, acetic acid and $H^+$ type ion exchange resin. These acids can be used singly or in combination thereof. The resultant compound can be dissolved or suspended in water or an organic solvent. Examples of the bases include sodium hydroxide, potassium hydroxide, lithium hydroxide, sodium carbonate, potassium carbonate, lithium carbonate, sodium hydrogen carbonate, potassium hydrogen carbonate, lithium hydrogen carbonate, calcium hydroxide, barium hydroxide, ammonia and primary, secondary and tertiary amines. Any reaction solvent can be used without particular limitation so long as it does not interfere with the reaction, but water and highly hydrophilic solvents are normally used. Examples of the hydrophilic solvents are acetone, methyl ethyl ketone, methanol, ethanol, n-propanol, isopropanol, acetonitrile, propionitrile, tert-butanol, dioxane, tetrahydrofuran, ethyl ether, ethylene glycol dimethyl ether, diethylene glycol dimethyl ether, ethyl acetate, dimethylformamide, dimethylacetamide, dimethylsulfoxide and hexamethylphosphoramide. These solvents can be used singly or in combination thereof. The reaction temperature ranges from $-10°$ C. to $120°$ C. and the reaction time ranges from about 1 to 20 hours.

Normally, a derivative in which $R_3'$ at the 5-position is hydrogen is used as a starting material.

Among the compounds (I), the intermediate of the amidated compound of the formula

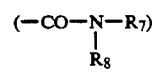

wherein $R_7$ and $R_8$ have the same meanings as defined above can be prepared by reacting ammonia or an amine of the formula (VI):

with the compound (III) (scheme 2).

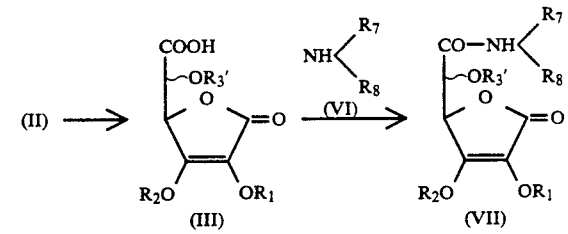

wherein $R_1$, $R_2$, $R_3'$, $R_7$ and $R_8$ have the same meanings as defined above. The compound (III) in the scheme 2 is prepared as described above.

The compound (VII) is prepared from the reaction of the compound (III) with the compound (VI) by a known method. For example, the reaction can be carried out using the carboxyl-activating reagent as described with respect to the thiol ester reaction.

The compound (III) may be converted into the corresponding acid halide as described above. Preferably, the resultant acid halide is reacted with the compound (VI) in an organic solvent in the presence of a base such as pyridine or triethylamine. The solvent are the same as those as described above. This amidation reaction can be performed at $-10°$ C. to $120°$ C. for about 1 to 5 hours.

When $R_1$ and/or $R_2$ in the compound (VII) are benzyl group optionally having substituents or $R_3'$ is an acyl group, these groups may be eliminated if required. The acyl group may be eliminated by the same manner as described above. Elimination of the benzyl group can normally be carried out by catalytic hydrogenation. Examples of the catalysts used for the catalytic hydrogenation include palladium, palladium chloride, platinum oxide, platinum black, ruthenium and the like. These catalysts may be supported on a carrier such as activated carbon, alumina, silica gel and the like. Any reaction solvent can be used without particular limitation so long as it does not interfere with the reaction. Examples of the solvents include methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water or the like. These solvents can be used singly or in combination thereof. The reaction temperature ranges from 10 to 100° C. and the reaction time is from 1 to 10 hours. The reaction can be carried out under ordinary or high pressure.

The derivative in which $R_3'$ at the 5-position is hydrogen is used as a starting material.

The compound (VIII) can be prepared by a known method disclosed in EP-A-0 295 842 or a method according to scheme 5 described hereinafter.

The compound (VII') can be prepared by reacting the compound (VIII) with the compound (VI) in an organic solvent under heating. Examples of the organic solvents are hydrocarbons such as hexane, benzene, toluene or the like, halogenated hydrocarbons such as chloroform, dichloromethane, 1,2-dichloroethane or the like, ethers such as diethyl ether, tetrahydrofuran, dioxane or the like, acetonitrile, dimethylformamide, dimethyl sulfoxide or the like. The reaction temperature ranges from 50° C. to 150° C. and the reaction time is about 5 to 20 hours.

When $-COR_4$ of the formula (I) is $-COO-R_5$, the compound (I) can also be prepared in accordance with the following schemes 4 and 5.

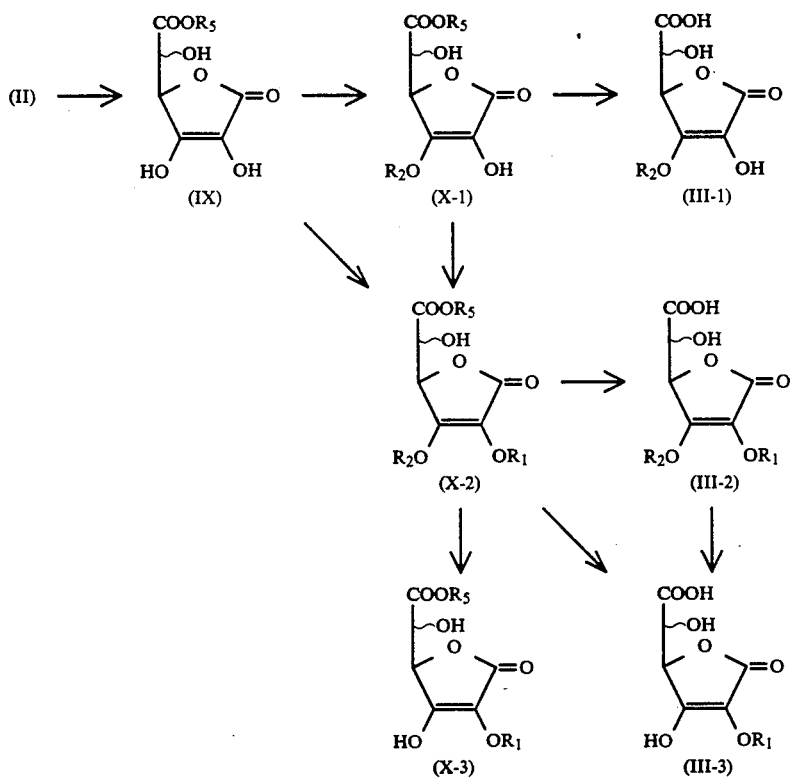

The intermediate of the amidated compound can be also prepared according to the scheme 3:

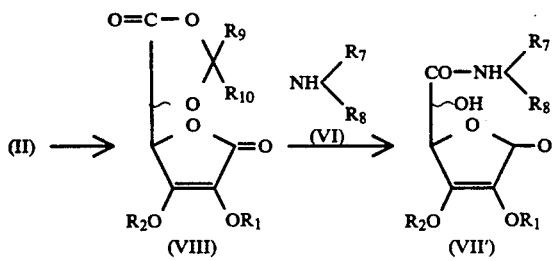

wherein $R_1$, $R_2$, $R_7$ and $R_8$ have the same meanings as defined above; and $R_9$ and $R_{10}$ each is, the same or different, hydrogen, methyl, ethyl, phenyl or $R_9$ and $R_{10}$ are combined to form $-(CH_2)_{4\sim 5}$.

wherein $R_1$, $R_2$ and $R_5$ are the same as defined above. As shown in the scheme 4, six kinds of saccharoascorbic acid derivatives, i.e., the compounds (III-1) to (III-3) and (X-1) to (X-3) can be prepared from the saccharoascorbic acid ester (IX) as a starting material. The compound (IX) can be prepared by a known method, e.g., the one disclosed in EP-A-0 295 842.

The compound (X-1) which is etherified at the 3-position can be prepared by the reaction of the compound (IX) with a compound represented by the formula $R_2X$ wherein $R_2$ has the same meaning as defined above and x is a halogen such as chlorine, bromine, iodine, etc., alkylsulfonyloxy such as methanesulfonyloxy, trifluoromethanesulfonyloxy, etc., arylsulfonyloxy such as benzenesulfonyloxy, p-toluenesulfonyloxy, etc., in the presence of an equivalent amount of a base.

The compound (III-1) can be obtained by hydrolyzing the ester at the 6-position of the compound (X-1). When $R_5$ of the compound (X-1) is a group which can be eliminated by reduction, the compound (III-1) can also be obtained by reduction.

The compound (X-2) which is etherified at the 2-position are prepared by the reaction of the compound (X-1) with a compound represented by the formula $$R_1X$$

wherein $R_1$ and X have the same meanings as defined above, in the presence of an equivalent amount of a base.

In the case where $R_1$ and $R_2$ are the same, the compound (X-2) can be prepared in one step from the compound (IX) by using two equivalent amounts of $R_1X$ and a base.

The compound (III-2) is obtained by hydrolyzing the ester at the 6-position of the compound (X-2). When $R_5$ of the compound (X-2) is a group which can be eliminated by reduction, the compound (III-2) can be obtained by reduction.

When $R_2$ of the compounds (X-2) and (III-2) is a group which can be eliminated by reduction, the compound (X-3) can be obtained from the compound (X-2) and the compound (III-3) from the compound (III-2).

Particularly, when $R_5$ and $R_2$ of the compound (X-2) are groups which can be eliminated by reduction or $R_2$ is a group which can be eliminated by hydrolysis, the compound (III-3) can be obtained from the compound (X-2) in one step by reduction or hydrolysis.

The free hydroxyl group at the 5-position of the resultant compound can be acylated by subjecting the compound to acylation reaction.

Examples of the group which can be eliminated by reduction include benzyl, p-methoxybenzyl, o-nitrobenzyl, p-nitrobenzyl, p-chlorobenzyl, p-bromobenzyl, p-cyanobenzyl, diphenylmethyl or the like.

Examples of the group which can be eliminated by hydrolysis include methoxymethyl, tert-butoxymethyl, 1-ethoxyethyl, 1-methyl-1-methoxyethyl or the like.

Each etherification is generally performed under the following conditions.

A base to be used for this reaction is not particularly limited. Examples of the bases are sodium hydride, calcium hydride, lithium hydride, lithium hydroxide, lithium hydrogen carbonate, lithium carbonate, sodium methoxide, sodium ethoxide, sodium hydroxide, sodium hydrogen carbonate, sodium carbonate, potassium hydroxide, potassium hydrogen carbonate, potassium carbonate, magnesium hydroxide, magnesium carbonate, calcium hydroxide, calcium carbonate, barium hydroxide, barium carbonate, pyridine, tertiary amines, substituted ammonium hydroxide $$(\equiv N^{\oplus}OH^{\ominus})$$

and the like.

Any reaction solvent can be used without any particular limitation so long as it does not interfere with the reaction, but normally a polar solvent is used. Examples of the solvents are acetonitrile, propionitrile, benzonitrile, formamide, dimethylformamide, dimethylacetamide, dimethyl sulfoxide, sulfolane, hexamethylphosphoramide, acetone, methyl ethyl ketone, dioxane, tetrahydrofuran, ethylene glycol dimethyl ether, diethylene glycol dimethyl ether, water or the like. These solvents can be used singly or in combination thereof. The reaction temperature ranges from 0° C. to 100° C., preferably from about 10° C. to 80° C. The reaction time is generally from 30 minutes to 4 days, although depending upon reactants, reaction reagents, reaction conditions and the like.

The hydrolysis of an ester at the 6-position and the hydrolysis of $R_2$ when $R_2$ is a group which can be eliminated by hydrolysis can generally be carried out under acidic conditions. Any acid can be used without particular limitation. Examples of the acids include hydrogen chloride, hydrogen bromide, hydrogen iodide, hydrogen fluoride, sulfuric acid, fluorosulfuric acid, perchloric acid, phosphoric acid, boric acid, p-toluenesulfonic acid, trifuloromethanesulfonic acid, methanesulfonic acid, trifluoroacetic acid, trichloroacetic acid, acetic acid, H+ type ion-exchange resins and the like. These substances may be used as they are, or dissolved or suspended in water or an organic solvent. These acids can be used singly or in combination thereof.

Any reaction solvent can be used without any limitation so long as it does not interfere with the reaction. Preferably, a hydrophilic solvent is normally used such as acetone, methyl ethyl ketone, methanol, ethanol, n-propanol, isopropanol, acetonitrile, propionitrile, tert-butanol, dioxane, tetrahydrofuran, ethyl ether, ethylene glycol dimethyl ether, diethylene glycol dimethyl ether, ethyl acetate, dimethylformamide, dimethylacetamide, dimethyl sulfoxide, hexamethylphosphoramide, water and the like. These solvents can be used singly or in combination thereof.

The reaction temperature ranges from 0° C. to 100° C., preferably about 10° C. to 80° C. The reaction time is generally about 1 to 10 hours, although depending upon reactant and reaction conditions.

The reduction can be performed by catalytic redution generally using hydrogen gas. Examples of the catalysts to be used for this reaction are palladium, palladium chloride, platinum oxide, platinum black, ruthenium, etc. These catalysts may be supported on a carrier such as activated carbon, alumina, silica gel and the like.

Any reaction solvent can be used without any limitation so long as it does not interfere with the reaction. Examples of the solvent are methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water and the like. These solvents can be used singly or in combination thereof.

The reaction temperature ranges from 10° C. to 100° C., and the reaction time is generally about 1 to 10 hours. The reaction may be conducted under atmospheric pressure or higher pressure.

The other preparation method is shown in the scheme 5.

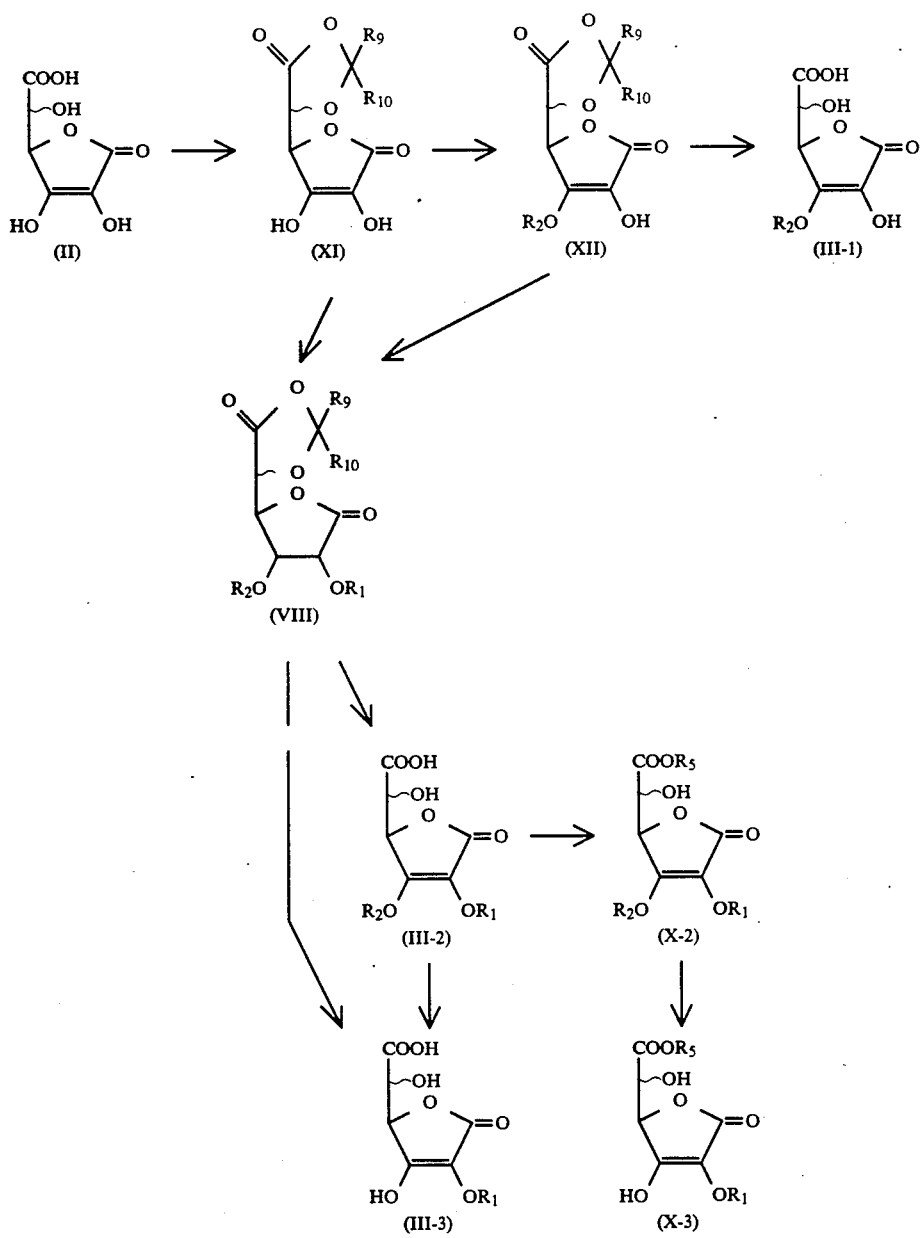

wherein $R_1$, $R_2$, $R_5$, $R_9$ and $R_{10}$ are the same as defined above.

As shown in the scheme 5, five kinds of saccharoascorbic acid derivatives, i.e., the compounds (III-1) to (III-3) and (X-2) and (X-3) can be prepared from the compound (XI). The compound (XI), which forms 4-oxo-1,3-dioxolane ring to protect at 5- and 6-positions of saccharoascorbic acid (II) can be prepared by a known method, e.g., the one disclosed in EP-A-0 295 842.

The compound (XII) which is etherified at the 3-position can be prepared by the reaction of the compound (XI) with a compound represented by the formula $R_2X$ wherein $R_2$ and X have the same meanings as defined above, in the presence of an equivalent amount of a base.

The compound (III-1) can be obtained by hydrolyzing the 4-oxo-1,3-dioxorane ring of the compound (XII).

The compound (VIII) can be prepared by the reaction of the compound (XII) with a compound represented by the formula $R_1X$ wherein $R_1$ and X have the same meanings as defined above, in the presence of an equivalent amount of a base.

In the case where $R_1$ and $R_2$ are the same substituents, the compound (VIII) can be prepared from the compound (XI) in one step by using two equivalent amounts of $R_1X$ and a base.

The compound (III-2) is obtained by hydrolyzing the compound (VIII). The compound (X-2) can be obtained by esterifying the carboxyl group at 6-position of the obtained compound (III-2).

When $R_2$ of the compounds (X-2) or (III-2) is a group which can be removed by reduction, the compounds (X-3) or (III-3) can be obtained from the compound (X-2) on the compound (III-2) by reduction as described above.

Particularly, when $R_2$ of the compound (VIII) is a group which can be eliminated by hydrolysis, the compound (III-3) can be obtained from the compound (VIII) in one step by hydrolysis.

The free hydroxyl group at the 5-position of the resultant compound can be acylated by subjecting the compound to acylation reaction.

Examples of the group which can be eliminated by reduction and hydrolysis are the same as those described above.

The step from the compound (II) to the compound (XI) is carried out by reacting the compound (II) with a ketone or aldehyde such as formaldehyde, acetaldehyde, acetone, propionaldehyde, methyl ethyl ketone, diethyl ketone, cyclopentanone, cyclohexanone, benzaldehyde or the like in the presence of an acid catalyst. Also, the compound (XI) can be obtained by reacting the compound (II) with a ketal or an acetal, which is respectively produced from the ketone or alkehyde with a lower alcohol.

Any reaction solvent can be used without any particular limitation so long as it does not interfere with the reaction, but normally a polar solvent is used. Examples of the solvents are acetonitrile, propionitrile, benzonitrile, nitromethane, nitroethane, nitrobenzene, dichloromethane, chloroform, carbon tetrachloride, 1,1-dichloroethane, 1,2-dichloroethane, hexane, cyclohexane, benzene, toluene, xylene, dioxane, tetrahydrofuran, 1,2-dimethoxyethane, ethylene glycol dimethyl ether, diethyl carbonate, dimethyl formamide, dimethyl sulfoxide or the like. The ketone, aldehyde, ketal and acetal can be used as a solvent. These solvents can be used singly or in combination thereof.

Examples of the acid catalysts include mineral acids such as hydrogen chloride, hydrogen bromide, hydrogen iodide, hydrogen fluoride, sulfuric acid, fluorosulfuric acid, perchloric acid, phosphoric acid or boric acid, organic acids such as p-toluenesulfonic acid, trifuloromethanesulfonic acid, methanesulfonic acid, trifluoroacetic acid, trichloroacetic acid, $H^+$ type ion-exchange resins and Lewis acids such as boron trifluoride, boron trichloride, boron tribromide, boron triiodide, aluminum chloride, titanium tetrachloride, zinc chloride, stannous chloride, stannic chloride and the like.

The reaction temperature ranges from 0° C. to 100° C., and the reaction time is generally about 1 to 24 hours.

The same reaction conditions as described before can be applied for the etherification, hydrolysis and reduction.

The step from the compound (III-2) to (X-2) can be carried out by a conventional esterification.

For example, (1) a direct esterification where the compound (III-2) is reacted with an alcohol represented by the formula $R_5OH$ (wherein $R_5$ has the same meaning as defined above) in the presence of an acid catalyst;

(2) a method via carboxylate where the compound (III-2) is reacted with a compound represented by the formula $R_5X$ (wherein $R_5$ and X have the same meanings as defined above) in the presence of a base;

(3) a method where the compound (III-2) is reacted with an alcohol represented by the formula $R_5OH$ (wherein $R_5$ has the same meaning as defined above) in the presence of a condensing reagent such as dicyclohexylcarbodiimide and the like;

(4) a method where the compound (III-2) is reacted with an olefinic compound such as isobutylene and the like in the presence of an acid catalyst; and (5) a method where the compound (III-2) is reacted with an O-alkylating agent such as diazomethane, orthoformic acid ester and the like.

The compound (X-2) shown in the schemes 4 and 5 are generally used as the starting material.

The saccharoascorbic acid derivatives produced by the methods of the present invention can easily be isolated by conventional methods such as extraction, chromatography (e.g., silica gel, polystyrene resin, activated charoal, reverse phase or normal phase chromatography) or recrystallization from the residue obtained after distillation of low boiling point substances such as the solvent from the reaction product.

A compound in which $R_3$ is a sulfo group in the compounds (I), i.e., 2,3-di-0-hydrocarbylsaccharoascorbic acid derivative 5-sulfate can be obtained by reacting 2,3-di-0-hydrocarbyl-5-hydroxysaccharoascorbic acid derivative, e.g, with a reactive derivative of sulfuric anhydride.

Examples of the reactive derivative of sulfuric anhydride include a complex such as sulfuric anhydride -pyridine, sulfuric anhydride-dioxane, sulfuric anhydride -trimethylamine, sulfuric anhydride-dimethylformamide or the like. Further, sulfuric anhydride or sulfuric anhydride -chlorosulfonate or the like is also usable.

Preferably, an inert solvent is used for this reaction such as dioxane, tetrahydrofuran, chloroform, dichloromethane, pyridine, dimethylformamide or the like.

The amount of the reactive derivative of sulfuric anhydride to be used is preferably 1.0 to 5.0 times the molar quantity of the corresponding 5-hydroxysaccharoascorbic acid derivative. The reaction temperature is preferably from 0° C. to 40° C. After the reaction, the reaction mixture is extracted with a solvent to isolate the 5-sulfate which is purified by a conventional method such as chromatography, recrystallization or the like.

A compound in which $R_3$ is a phosphono group in the compound (I), i.e., 2,3-di-0-hydrocarbylsaccharoascorbic acid derivative 5-phosphate can be obtained by reacting 2,3-Di-0-hydrocarbyl-5-hydroxysaccharoascorbic acid derivative with a suitable phosphorylating reagent.

Examples of the phosphorylating reagents used for the reaction include orthophosphoric acid anhydrous, methaphosphoric acid, phosphorus pentoxide, phosphorus oxychloride, pyrophosphoryl tetrachloride, tetra-p-nitrophenyl pyrophosphate, phosphorodimorpholidic chloride, o-phenylenephosphorochloridate, diphenylphosphorochloridate, di-p-nitrobenzylphosphorochloridate or the like. The phosphorylating reagent may be used singly or reacted with a base of about equivalent amount or excess amount in a solvent.

Examples of the bases are organic bases such as pyridine, 2,6-lutidine, picoline, triethylamine, N-methylmorpholine or the like or inorganic bases such as sodium hydroxide, potassium hydroxide, sodium hydrogen carbonate, sodium carbonate or the like.

Examples of the solvents are water, acetone, acetonitrile, dioxane, N,N-dimethylformamide, tetrahydrofuran, dichloromethane, or a mixture thereof.

The amount of the phosphorylating agent to be used is preferably 1.0 to 5.0 equivalents to the corresponding 5-hydroxysaccharoascorbic acid derivative. The reaction temperature is preferably from 0° C. to 40° C.

After the reaction, when the phosphorylating agent having a protecting group is used, its protecting group is removed by a known method. The reaction mixture is then extracted with a solvent to obtain the 5-phosphate or its salt having a desired purity by a conventional method such as chromatography, recrystallization or the like.

Examples of a salt of the sulfo group or phosphono group in the compound (I) are inorganic salts such as lithium, potassium, sodium, calcium, ammonium or the like and organic salts such as pyridine, collidine, triethylamine or the like.

The compounds of the present invention are not limited to these salts. The free forms thereof are included in the present invention. The compounds obtained in the form of salt can be converted into free forms by, for example, a strong acidic cation exchange resin.

The compounds represented by the formula (I) or salts thereof may be amorphous or crystalline forms.

The pharmaceutical composition useful for preventing and treating thrombosis of the present invention comprises the saccharoascorbic acid derivative (I) or salt thereof itself, or optionally together with a pharmaceutically acceptable carrier or diluent and can be administered orally or parenterally.

Compositions for oral administration may be solid or liquid forms, specifically tablets (including sugar coated tablest and film coated tablets), pills, granules, powders, capsules (including soft capsules), syrups, elixir, emulsions and suspensions which can be prepared by the conventional method. Such compositions will contain conventional carriers or excipients and can be prepared by known methods. Examples of carriers or excipients include binders such as syrup, gum arabic, gelatine, sorbitol, tragacanth gum, polyvinyl pyrrolidone or the like; fillers such as lactose, sugar, corn starch, calcium phosphate, glycine or the like; lubricants such as magnesium stearate, talc, polyethylene glycol, silica or the like; disintegrators such as potato starch or wetting agents such as sodium lauryl sulfate.

Compositions for parenteral administration are, e.g., injections and suppositories, the former of which includes subcutaneous, intracutaneous, intramuscular or like injections. Such injections can be prepared by suspending or emulsifying the compound (I) or its salt in or with sterile aqueous or oily liquids which are usually employed in injections, in accordance with the methods known in the art. Examples of the aqueous liquids for injections are physiological saline and isotonic solution, which may be used together with a suitable suspending agent such as sodium carboxy methylcellulose or a nonionic surfactant upon circumstances. Examples of the oily liquids are sesame oil and soybean oil, which may be used together with a solubilizing agent such as benzyl benzoate or benzyl alcohol. The injections thus prepared are usually put into ampoules.

The pharmaceutical composition useful for preventing and treating thrombosis of the present invention can be administered in an amount sufficient for manifesting the desired prophylactic and therapeutic effects in the human body. The amount varies depending upon the age and body weight of a particular patient as well as a particular administration route, dosage form and the like.

For example, the pharmaceutical composition of the present invention can be administered orally or parenterally to an adult patient in a daily dosage of 0.1 to 100 mg/kg, preferably 1 to 50 mg/kg in terms of mg of the compound (I) or a pharmaceutical acceptable salt thereof per kg of the adult patient, 1 to 6 times a day.

Toxicity of the saccharoascorbic acid derivatives of the present invention is low, so that they can be advantageously used as a therapeutic agent.

The saccharoascorbic acid derivative of the present invention can promote and/or induce the production of plasminogen activator by vascular endothelial cells to accelerate fibrinolysis and, therefore, it can be used for preventing and treating thrombosis.

The following Preparations and Examples further illustrate the present invention in detail but are not to be construed to limit the scope thereof.

REFERENCE EXAMPLE 1

2,3-Di-O-benzyl-D-glucosaccharoascorbic acid n-octadecanethiolester

5-O-Acetyl-2,3-di-O-benzyl-D-glucosaccharoascorbic acid (4.98g) prepared according to the method disclosed in EP-A-0 296 842 was dissolved in dichloromethane (30 ml). Phosphorous pentachloride (2.59 g) was added to the solution and the mixture was stirred at room temperature for 30 minutes. The mixture was distilled under reduced pressure to remove low boiling point substances, thereby affording the acid chloride as a paste.

The acid chloride was dissolved in dichloromethane (20 ml). To the solution was added dropwise a solution of n-octadecyl mercaptan (3.40 g) in dichloromethane (5 ml) with ice-cooling.

Subsequently, a mixture of triethylamine (1.20 g) and dichloromethane (3 ml) was slowly added dropwise and the resulting mixture was stirred for 4 hours.

The reaction mixture was poured into water (100 ml) and extracted 3 times with dichloromethane. After drying, the extract was distilled to remove the solvent and the residue was chromatographed on a silica gel column (solvent: ethyl acetate - hexane = 1 : 5) to obtain crude crystals of 5-O-acetyl-2,3-di-O-benzyl-D-glucosaccharoascorbic acid n-octadecanethiolester (2.97 g).

Yield: 36.8%

Melting point: 61°–62° C. (recrystallized from hexane)

IR (KBr) cm$^{-1}$: 1770, 1750, 1685, 1670

$^1$H-NMR (CDCl$_3$)δ: 0.88(t,3H), 1.10–1.60(m,32H), 5.11(d,1H), 5.20(s,2H), 5.72(d,1H,J=3Hz), 7.13–7.38(m,10H)

MS: m/e 680(M), 620, 588

Elemental Analysis for C$_{40}$H$_{56}$O$_7$S:

Calc. (%): C, 70.55; H, 8.29.

Found (%): C, 70.47; H, 8.27.

5-O-Acetyl-2,3-di-O-benzyl-D-glucosaccharoascorbic acid n-octadecanethiolester (2.97 g) thus prepared was dissolved in a mixture of 2N sulfuric acid (20 ml) and acetonitrile (100 ml) and the solution was refluxed for 20 hours. After the completion of the reaction, the mixture was distilled to remove acetonitrile. Water (50 ml) was added to the residue and the mixture was extracted three times with dichloromethane.

After drying, the extract was distilled to remove the solvent and the residue was chromatographed on a silica gel column (solvent: ethyl acetate-hexane=1:5) to obtain 2,3-di-O-benzyl-D-glucosaccharoascorbic acid n-octadecanethiolester (2.67 g).

Yield: 95.8%

Melting point: 55°-56° C. (recrystallized from hexane)

IR (KBr) cm$^{-1}$: 3600-3300, 1770, 1670

$^1$H-NMR (CDCl$_3$)δ: 0.88(t,3H), 1.08-1.53(m,32H), 2.68(m,2H), 4.67(d,1H,J=2Hz), 5.00-5.17(m,5H), 7.09-7.38(m,10H)

Figuring for OH was difficult because the band for OH was very broad.

MS: m/e 633(M), 570, 546

Elemental Analysis for C$_{38}$H$_{54}$O$_6$S:

Calc. (%): C, 71.44; H, 8.52.

Found (%): C, 71.45; H, 8.56.

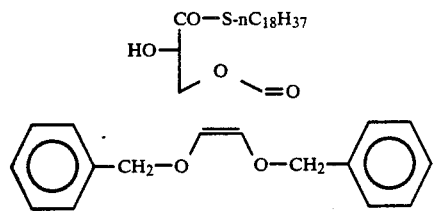

REFERENCE EXAMPLE 2

5-O-Acetyl-2,3-di-O-benzyl-D-glucosaccharoascorbic acid n-octadecylamide

5-O-Acetyl-2,3-di-O-benzyl-D-glucosaccharoascorbic acid (5.00g) was dissolved in dichloromethane (40 ml). Phosphorous pentachloride (2.77 g) was added to the solution and the mixture was stirred at room temperature for 30 minutes. The mixture was distilled off under reduced pressure to remove low boiling point substances, thereby affording the acid chloride as a paste.

The acid chloride was dissolved in dichloromethane (30 ml). To the solution were added dropwise a solution of n-octadecylamine (3.40 g), triethylamine (1.20 g) and dichloromethane (150 ml) with ice-cooling.

The reaction mixture was poured into water (200 ml) and extracted 3 times with dichloromethane. The combined extracts were dried over anhydrous sodium sulfate and distilled to remove the solvent. The residue was chromatographed on a silica gel column (solvent: ethyl acetate-hexane=1:1) to obtain 5-O-acetyl-2,3-di-O-benzyl-D-glucosaccharoascorbic acid n-octadecylamide (6.10 g).

Yield: 75.8%

Melting point: 51°-53° C. (recrystallized from dichloromethane-hexane= 1 : 4)

IR (KBr) cm$^{-1}$: 3320, 1790, 1750, 1690, 1670

$^1$H-NMR (DMSO-d$_6$)δ: 0.85(t,3H), 1.10-1.40(m,32H), 2.10(s,3H), 2.90-3.15(m,2H), 4.94(s,2H), 5.18-5.40(m,4H), 7.25-7.42(m,10H), 8.00(br.NH)

Elemental Analysis for C$_{40}$H$_{57}$NO$_7$:

Calc. (%): C, 72.37; H, 8.65; N, 2.11.

Found (%): C, 72.49; H, 8.87; N, 2.15.

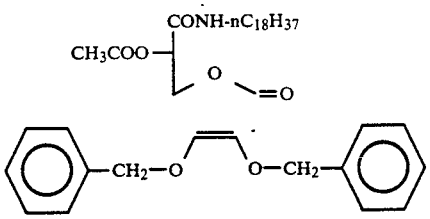

REFERENCE EXAMPLE 3

2,3-Di-O-benzyl-D-glucosaccharoascorbic acid n-octadecylamide

5-O-Acetyl-2,3-di-O-benzyl-D-glucosaccharoascorbic acid n-octadecylamide (5.90 g) prepared in Reference Example 2 was dissolved in a mixture of 2N sulfuric acid (20 ml) and acetonitrile (60 ml). The resultant mixture was heated under reflux for 12 hours. Thereafter, acetonitrile was distilled off and water (200 ml) was added to the residue. The reaction mixture was extracted 3 times with dichloromethane. The combined extracts were dried over sodium sulfate and distilled to remove the solvent. The residue was chromatographed on a silica gel column (solvent: ethyl acetate-hexane=1:1) to obtain 2,3-di-O-benzyl-D-glucosaccharoascorbic acid n-octadecylamide (3.50 g).

Yield: 63.3%

Melting point: 105°-107° C.

IR (KBr) cm$^{-1}$: 3500-3200, 1755, 1685, 1645

$^1$H-NMR (DMSO-d$_6$)δ: 0.85(t,3H), 1.04-1.28(m,32H), 2.83-3.03(m,2H), 4.30(m 1H), 4.95(s,2H), 5.10-5.20(m,3H), 6.37(d,OH), 7.18-7.42(m,10H), 7.66(br.NH)

Elemental Analysis for C$_{38}$H$_{55}$NO$_6$:

Calc. (%): C, 73.40; H, 8.91; N, 2.25.

Found (%): C, 73.62; H, 8.93; N, 2.22.

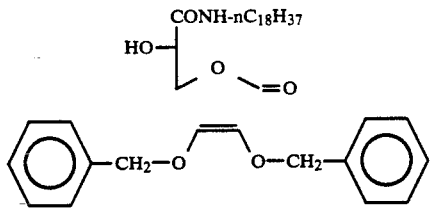

EXAMPLE 1

2,3-Di-O-benzyl-5-O-sulfo-D-glucosaccharoascorbic acid n-octadecanethiolester sodium salt 2,3-Di-O-benzyl-D-glucosaccharoascorbic acid n-octadecanethiolester (640 mg) prepared by Reference Example 1 was dissolved in anhydrous dimethylformamide (DMF) (2 ml) and ice-cooled. To this solution was added 1.25M DMF-SO$_3$ complex/DMF solution (4 ml) (5 equivalents). The resultant solution was stirred for an hour at room temperature and distilled under reduced pressure to remove DMF. To the residue was added an aqueous saturated sodium hydrogen carbonate solution under ice-cooling to adjust to PH 7. The resultant turbid solution was subjected to Amberlite ® XAD-II column chromatography (40φ×300 mm, porous polymer of styrene and divinylbenzene, Rohm &

Haas Co.), eluting with water and methanol successively. The object fractions were concentrated under reduced pressure. The concentrate was dissolved into water and lyophilized to afford amorphous powders of 2,3-di-O-benzyl-5-O-sulfo-D-glucosaccharoascorbic acid n-decanethiolester sodium salt (710 mg).

Yield: 96.0%

IR (KBr) cm$^{-1}$: 1770(shoulder), 1760, 1675, 1270, 1060, 1040

$^1$H-NMR (DMSO-d$_6$)δ: 0.86(t,3H), 1.0–1.53(m,32H), 2.72(m,2H),4.80–5.00(m,3H), 5.10–5.40(m,3H), 7.20–7.50(m,10H)

Elemental Analysis for C$_{38}$H$_{53}$O$_9$S$_2$Na 1.0H$_2$O:
Calc. (%): C, 60.14; H, 7.30.
Found (%): C, 60.38; H, 7.50.

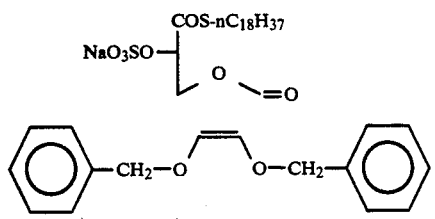

EXAMPLE 2

2,3-Di-O-benzyl-5-O-phosphono-D-glucosaccharoascorbic acid n-octadecanethiolester sodium salt 2,3-Di-O-benzyl-D-glucosaccharoascorbic acid n-octadecanethiolester (1 g) was dissolved in anhydrous tetrahydrofuran (2 ml). To this solution was added pyrophosphoryl tetrachloride (1 ml) (4.5 equivalents). The mixture was allowed to react for 15 hours at room temperature. The reaction solution was dropwise added to a cube of ice (20 g) for hydrolysis. Thereafter, the resultant mixture was adjusted to pH 7.5 with 1N sodium hydroxide solulion. The resultant solution was concentrated to about 30 ml under reduced pressure. The concentrated solution was subjected to Amberlite ® XAD-II column chromatography (40φ×300 mm, Rohm & Haas Co.), eluting with water, 70% methanol, 80% methanol and 90% methanol successively. The object fractions was lyophilized to afford hygroscopic colorless powders of 2,3-di-O-benzyl-5-O-phosphono-D-glucosaccharoascorbic acid n-octadecanethiolester sodium salt (530 mg).

Yield: 46.0%

IR (KBr) cm$^{-1}$: 1770, 1680, 1060, $^1$H-NMR (CD$_3$OD)δ: 0.90(t,3H), 1.10–1.60(m,32H), 2.75(m,2H),4.96(s,2H), 5.05–5.30(m,4H), 7.20–7.50(m,10H)

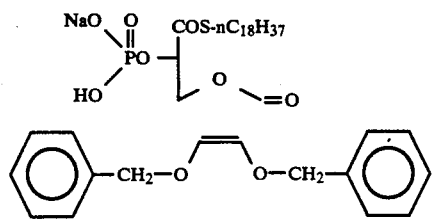

EXAMPLE 3

2,3-Di-O-benzyl-5-0-phosphono-D-glucosaccharoascorbic acid n-octadecanethiolester sodium salt 2,3-Di-O-benzyl-D-glucosaccharoascorbic acid n-octadecanethiolester (6.4 g) was dissolved in toluene (50 ml). To this solution were added phosphorus oxychloride (3.7 ml) and 2.6-lutidine (2.3 ml) successively under ice-cooling and stirring. The resultant mixture was stirred for an hour at room temperature. Thereafter, the precipitated crystals were filtered off and the filtrate was concentrated under reduced pressure. To this concentrate were added ethyl acetate (25 ml) and ice water (25 ml) under ice-cooling, while vigorously stirring. The ethyl acetate layer was collected and then poured into an ice-cooled solution of sodium hydrogen carbonate (5 g) in water (25 ml). The reslutant mixture was stirred for 2 hours at room temperature and ice-cooled. Thereafter, the reslutant mixture was adjusted to pH 4.5 with acetic acid (5 ml), subjected to Amberlite ® XAD-II column chromatography (40φ×300 mm, Rohm & Haas Co.), eluting with water (100 ml), 20% methanol (1000 ml) and 90% methanol (1300 ml) successively. The object fractions were concentrated under reduced pressure and lyophilized to afford an amorphous product (4.6 g). The obtained amorphous product was dissolved into ethanol (5 ml) and the solution was left for 3 hours under ice-cooling. The precipitated crystals were collected and dried (3.9 g). Subsequently, the resultant crystals were dissolved into dichloromethane (20 ml), to which ethanol (10 ml) was added. The resultant mixture was concentrated at 20° C. under reduced pressure to collect precipitated crystals. The obtained crystals were washed with cooled ethanol and dried under reduced pressure to afford 2,3-di-O-benzyl-5-phosphono-D-glucosaccharoascorbic acid n-octadecanethiolester sodium salt (3.2 g).

Elemental Analysis for C$_{38}$H$_{54}$O$_9$SNaP:
Calc. (%): C, 61.66; H, 7.35; S, 4.33; P, 4.18:
Found (%): C, 61.36; H, 7.48; S, 4.40; P, 4.12.

$^1$H-NMR (400MHz,DMSO-d$_6$)δ: 0.85(t,J=6.6Hz,CH$_3$), 1.17–1.30(C$_{15}$H$_{30}$), 1.41(quintet,J=7Hz, SCH$_2$CH$_2$), 2.64, 2.72 (each dt,J=13.3,7.0, 7.0,SCH$_2$), 4.87(dd, J=2Hz, J$_{POCH}$=10.5Hz, 5-H), 4.93(s,CH$_2$Ph), 5.30 and 5.23(ABq, J=11.7Hz,CH$_2$Ph), 5.30 (d,J=2Hz,4-H), 7.30–7.43(m,Ph)

IR(KBr)cm$^{-1}$: 2920, 2850, 1770, 1670, 1460, 1410, 1360, 1315, 1150, 1100, 1055, 940, 910, 875, 810, 740, 705, 695, 675, 590, 570, 555,500

[α]$_D$= −40.6° (c=0.9 in CHCl$_3$)
[α]Hg365= −227.2° (c=0.9 in CHCl$_3$)
mp: 130°–134° C.

EXAMPLE 4

2,3-Di-O-benzyl-5-O-phosphono-L-gulosaccharoascorbic acid n-octadecanethiolester sodium salt 2,3-Di-O-benzyl-D-glucosaccharoascorbic acid n-octadecanethiolester (6.4 g) was dissolved in toluene (50 ml). To this solution were added phosphorus oxychloride (3.7 ml) and pyridine (2.3 ml) successively under ice-cooling and stirring. The resultant mixture was stirred for an hour at room temperature. Thereafter, the precipitate was filtered off and the filtrate was concentrated under reduced pressure. To the residue were added ethyl acetate (25 ml) and ice water (25 ml) under ice-cooling, while vigorously stirring. The ethyl acetate layer was collected and then poured into a solution of ice-cooled solution of sodium hydrogen carbonate (5 g) in water (25 ml). The reslutant mixture was stirred for 2 hours at room temperature and ice-cooled. After adjusting to pH 4.5 with acetic acid (5ml), the reslutant mixture was chromatographed on Amberlite® XAD-II column chromatography (40φ×300 mm, Rohm & Haas Co.) eluting with water (100 ml), 20% methanol (1000 ml) and 90% methanol (1300 ml) successively. After eluting the fraction of 2,3-di-O-benzyl-5-O-phosphono-D-glucosaccharoascorbic acid sodium salt, the remaining L-gulosaccharoascorbic acid derivative was eluted with methanol. The eluate was concentrated under reduced pressure and the residue was recrystallized from methanol to afford 2,3-di-O-benzyl-5-O-phosphono-L-gulosaccharoascorbic acid n-octadecanethiolester sodium salt (1.5 g).

Elemental Analysis for $C_{38}H_{54}O_9SNaP$:
Calc. (%): C, 61.66; H, 7.35; S, 4.33; P, 4.18:
Found (%): C, 61.81; H, 7.57; S, 4.05; P, 3.96.
$^1$H-NMR (400MHz,DMSO-$d_6$)$\delta$: 0.84(t,J=6.8Hz,$CH_3$), 1.17–1.30 ($C_{15}H_{30}$), 1.36(quintet,J=7.1Hz, $SCH_2\underline{CH_2}$), 2.57, 2.68 each dt,J=13.2, 7.3, 7.3,$\underline{SCH_2}$), 4.87 and 4.89(ABq,J=11.2Hz, $\underline{CH_2}Ph$), 5.05(5-H), 5.21 and 5.27(ABq,J=12Hz, $\underline{CH_2}Ph$), 5.51 (d,J=2.2Hz, 4-H), 7.30–7.43(m,Ph)

IR(KBr)$cm^{-1}$: 2920, 2850, 1790, 1765, 1680, 1660, 1470, 1455, 1340, 1315, 1250, 1150, 1125, 1095, 1060, 955, 890, 740, 695, 520
$[\alpha]_D^{25°} = -24.7°$ (c=0.5075 in $CHCl_3$)
$[\alpha]Hg365^{25°} = -147.7°$ (c=0.5075 in $CHCl_3$) mp: 190° C.

EXAMPLE 5

A mixture of 2,3-di-O-benzyl-5-O-phosphono-D-glucosaccharoascorbic acid n-octadecanethiolester sodium salt as prepared by Example 3 (300 mg), sodium chloride (9 g) and benzyl alcohol (9 g) was dissolved in distilled water for injection to make the total amount to 1000 ml. This solution was aseptically filtered through a membrane filter (mesh: 0.2μm). The filtrate was aseptically packed into a vial (volume: 50 ml) which was then stopped with a rubber cap and further with an aluminum screw cap to prepare injection.

EXAMPLE 6

2,3-di-O-benzyl-5-O-phosphono-D-glucosaccharoascorbic acid n-octadecanethiolester sodium salt as prepared by Example 3 (400 mg), lactose (195 mg) and magnesium stearate (5 mg) were well mixed and packed into gelatine hard capsule to make capsules, in accordance with a conventional method.

EXAMPLE 7

Determination of Capability of Induction of Plasminogen Production by Using Vascular Endothelial Cells Activities of saccharoascorbic acid derivatives for the induction of plasminogen activator production by cultivated bovine lung aorta endothelial cells were determined by using plasminogen-containing fibrin plate method.

(1) Materials (a) Bovine lung aorta endothelial cells
Bovine lung aorta endothelial cells CCL 209 purchased from American Type Culture Collection were used.

(b) Culture medium
Used culture medium was Dulbecco's modified minimum essential medium containing 10% inactivated bovine fetal serum, penicillin G(100 U/ml) and streptomycin (100μg/ml).

(c) Fibrinogen solution
Bovine fibrinogen containing 75% clottable protein (manufactured by Seikagaku Kogyo Co., Ltd., Japan) was dissolved in phosphate buffer (50 mM, pH 7.4) and the solution was applied on a lysine Sepharose column. The fraction passed through the column was collected to obtain a fibrinogen free from both plasmin and plasminogen. The fibrinogen fraction thus obtained was diluted with phosphate buffer to have the fibrinogen concentration of 10 mg/ml.

(d) Thrombin solution
Bovine thrombin (1000 units/vial, manufactured by Mochida Seiyaku Co., Ltd., Japan) was dissolved in physiological saline so that the concentration thereof became 10 units/ml.

(e) Plasminogen solution
Human plasminogen (51.5 units/vial, Nihon Pharmaceutical Co., Ltd., Japan) was dissolved in physiological saline so that the concentration thereof became 10 units/ml.

(f) Agarose solution
Agarose (Seakem ME manufactured by FMC Corporation, U.S.A.) was dissolved in Tris-HCl buffer (50 mM, pH 7.5)-12 mM NaCl so that the concentration thereof became 1% (W/V).

(g) Gel bond film
Gel bond film for agarose (manufactured by FMC corporation, U.S.A.) cut into a rectangle (8.0 cm×12.5 cm) was used.

(h) Authentic human urokinase solution
Human urokinase (protein content: 0.88 mg/ml, manufactured by Nihon Pharmaceutical Co., Ltd., Japan) was diluted with Tris-HCl buffer (50 mM, pH 7.5)-12 mM NaCl containing 0.1% bovine serum albumin to prepare solutions having the urokinase concentrations of 50, 25, 12.5, 6.25 and 3.125 ng/ml, respectively.

(2) Determination (a) Method for cultivation of bovine lung aorta endothelial cells and induction of plasminogen activator production by addition of saccharo
ascorbic acid derivatives A suspension of bovine lung aorta endothelial cells (number of subcultures: 21 to 26) was placed in each well of a plate having 96 wells (manufactured by A/S Nunc, Roskilde, Denmark) in an amount of 3,000 cells/100μl/well and cultivated in an incubator containing 5% $CO_2$/95% air at 37° C. for 3 days to grow the cells in a pre-confluent state. After removing the culture medium, the cells were washed with PBS (−) and, again, 95μl/well of the fresh culture medium was added.

A saccharoascorbic acid derivative was dissolved in dimethyl sulfoxide (DMSO) to have a concentration of 10 mM. The solution was diluted 10, 100 and 1000 times with the culture medium to obtain 1, 0.1 and 0.01 mM solutions, respectively. As the controls, DMSO was diluted 10, 100 and 1000 times with the culture medium. The diluted saccharoascorbic acid derivative and the controls were added to the 96-well plate in an amount of 5μl/well so that the final concentrations became 50, 5 and 0.5 μM. The plate was incubated for 2 days. After incubation, the supernatant of the culture was collected to be used as the sample for determination of plasminogen activator activity.

(b) Preparation of fibrin plate containing plasminogen and determination of plasminogen activator activity To the solution of bovine fibrinogen solution (3 ml) was added the human plasminogen solution (0.5 ml). After maintained at 50° C. for 2 minutes, the mixture was admixed with the agarose solution (10 ml) which had been dissolved with heating and maintained at 50° C. Immediately, the bovine thrombin solution (0.1 ml) was added thereto. The whole mixture was cast on the gel bond film and allowed to stand at room temperature for an hour to obtain fibrin plate.

Holes of 3 mm in diameter were provided on the plate, to which the sample (5 µl) and the authentic human urokinase solution (5 µl) were added. After the reaction at 37° C. for 6 hours, the diameter of the resulting lysis spot was measured to determine plsminogen activator activity of the sample from a calibration curve.

(3) Results

Table 1 shows the capabilities of induction of the plasminogen activator production by the saccharoascorbic acid derivatives obtained in Examples 1 and 2.

TABLE 1

| Compound | Concentration (µM) | Plasminogen Activator Activity (ng/ml) |
|---|---|---|
| Example 1 | 50 | 18.5 |
|  | 5 | 13.4 |
|  | 0.5 | 6.7 |
| Example 2 | 50 | 21.3 |
|  | 5 | 15.5 |
|  | 0.5 | 8.6 |
| Control | — | 3.1 |

As seen from Table 1, plasminogen activator activities are increased, at most, 7 times that of the control by the addition of the saccharoascorbic acid derivatives.

EXAMPLE 8

Enhancement of Plasmin Activity by Intravenous Administration to Rats 2,3-Di-O-benzyl-5-O-sulfo-D-glucosaccharoascorbic acid n-octadecanethiolester sodium salt obtained by Example 1 was intravenously administered to rats. Blood was collected with time to prepare euglobulin fractions. The plasmin activity thereof was determined.

(1) Materials (a) Animals

Used animals were male Sprague-Dawley rats (10–12 week old, body weight: 370–450 g; CLEA Japan Inc., Japan).

(b) S-2251 solution 3 mM solution of S-2251 (H-D-Val-Leu-Lys-pNA, AB Kabi, Sweden) was dissolved in distilled water.

(2) Administration Method

A sample was dissolved in physiological saline in an amount of 0.5, 1.5, 5 and 25 mg/ml. Each solution was intravenously administered to a rat anesthetized with ether in an amount of 1, 3, 10 and 50 mg/Kg.

(3) Determination of Plasmin Activity (a) Preparation of a euglobulin fraction

To blood (9 parts by volume) collected was added 3.8% sodium citrate solution (1 part by volume). The mixture was centrifuged at 3,000 r.p.m. for 10 minutes. The resulting supernatant (0.5 ml) was adjusted to pH 5.2 with cold 0.017 % acetic acid solution (9.5 ml), followed by being left at 4° C. for 30 minutes. The precipitate was collected by centrifugation and dissolved in 0.05M Tris-HCl buffer (pH 7.5)-0.012M NaCl (0.5 ml) to obtain a euglobulin solution.

(b) Determination of activity for hydrolyzing S-2251

To the euglobulin solution (0.25 ml) were added 0.05M Tris-HCl buffer (pH 7.5)-0.012M NaCl (0.23 ml), and the mixture was incubated at 37° C. for 30 minutes. Then, 50% acetic acid solution (0.05 ml) was added to the reaction mixture to terminate the reaction. Thereafter, the absorbance at the wavelength of 405 nm was measured.

According to the above method, the compound obtained by Example 1 was administered intravenously to rats (3 rats/group) at doses of 1, 3, 10 and 50 mg/kg). The plasmin activity in blood was determined with time. Table 2 shows the average values of the results.

TABLE 2

|  | Blood collection time (min) | Plasmin activity in blood ($\Delta A_{405} \times 10^3$/min) |
|---|---|---|
| Administration group (50 mg/kg) | 10 | 23.2 |
|  | 30 | 21.5 |
|  | 60 | 25.3 |
| Administration group (10 mg/kg) | 10 | 13.0 |
|  | 30 | 8.4 |
|  | 60 | 6.2 |
| Administration group (3 mg/kg) | 10 | 5.0 |
|  | 30 | 4.3 |
|  | 60 | 2.5 |
| Administration group (1 mg/kg) | 10 | 3.4 |
|  | 30 | 3.0 |
|  | 60 | 2.3 |
| Control group | 10 | 3.6 |
|  | 30 | 2.4 |
|  | 60 | 3.4 |

As seen from Table 2, plasmin activities in blood were remarkably increased in the administration groups adn reached to, at highest, 8 times as high as that of the control group.

EXAMPLE 9

Enhancement of Plasmin Activity by Intravenous Administration to Rats 2,3-Di-O-benzyl-5-O-phosphono-D-glucosaccharoascorbic acid n-octadecanethiolester sodium salt obtained by Example 2 was intravenously administered to rats. Blood was collected with time to prepare euglobulin fractions. The plasmin activity thereof was determined.

(1) Materials (a) Animals

Used animals were male Sprague-Dawley rats (10–11 week old, body weight: 400–460 g; CLEA Japan Inc., Japan).

(b) S-2251 solution

The same solution as prepared in Example 8 was used.

(2) Administration Method

The administration was performed in accordance with the same manner as in Example 8.

(3) Determination of Plasmin Activity

The determination was performed in accordance with the same manner as in Example 8.

According to the above method, the compound obtained in Example 2 was administered intravenously to rats (3 rats/group) at doses of 1, 3, 10 and 50 mg/kg. The plasmin activity in blood was determined with time. Table 3 shows the average values of the results.

TABLE 3

| | Blood collection time (min) | Plasmin activity in blood ($\Delta A_{405} \times 10^3$/min) |
|---|---|---|
| Administration group (50 mg/kg) | 10 | 22.1 |
| | 30 | 15.3 |
| | 60 | 12.4 |
| Administration group (10 mg/kg) | 10 | 9.7 |
| | 30 | 7.4 |
| | 60 | 2.6 |
| Administration group (3 mg/kg) | 10 | 4.3 |
| | 30 | 3.0 |
| | 60 | 3.5 |
| Administration group (1 mg/kg) | 10 | 4.1 |
| | 30 | 4.1 |
| | 60 | 3.9 |
| Control group | 10 | 3.4 |
| | 30 | 2.0 |
| | 60 | 1.7 |

As seen from Table 3, plasmin activities in blood were remarkably increased in the administration groups adn reached to, at highest, 7 times as high as that of the control group.

EXAMPLE 10

Enhancement of Plasmin Activity by Intravenous Administration to Rats 2,3-di-O-benzyl-5-O-phosphono-D-glucosaccharoascorbic acid n-octadecanethiolester sodium salt obtained by Example 2 was intravenously administered to rats. Blood was collected from carotid arteries 1 minute after the administration to prepare euglobulin fractions. The clot lysis time of the whole blood and plasmin activity of the euglobulin fractions were determined.

(1) Materials (a) Animals

Used animals were male Sprague-Dawley rats (13 week old, body weight: 410–490 g; CLEA Japan Inc., Japan).

(b) S-2251 solution

The same solution as prepared in Example 8 was used.

(2) Administration Method

A smaple was dissolved in physiological saline at an amount of 0.05, 0.5 and 5 mg/ml. Thereafter, each solution was intravenously administered to a rat anesthetized with sodium pentobarbital (40 mg/kg) in an amount of 0.1, 1 and mg/kg.

(3) Determination of Plasmin Activity (a) Preparation of a euglobulin fraction A euglobulin fraction was prepared by the same manner as in Example 8.

(b) Determination of activity for hydrolyzing S-2251

The activity for hydrolyzing S-2251 was determined by the same manner as in Example 8.

(c) Determination of clot lysis time of whole blood

A clot lysis time of whole blood was determined by the method disclosed in British Journal of Pharmacology, 93, 156 (1988). Specifically, blood was added to a test tube containing 0.12M sodium acetate (1.7 ml) and 20 units/ml thrombin (0.1 ml), followed by incubating at 37° C to prepare a clot. The time required for lysing the clot was measured.

According to the above method, the compound obtained by Example 1 was administered intravenously to rats (5 rats/group) at doses of 0.1, 1 and 10 mg/kg). Blood was collected from carotid arteries in an amount of 2 ml 1 minute after the administration. The plasmin activity in blood and clot lysis time of whole blood were determined. Table 4 shows the average values of the results.

TABLE 4

| | Plasmin activity in blood ($\Delta A_{405} \times 10^3$/min) | clot lysis time of whole blood (min) |
|---|---|---|
| Administration group (10 mg/kg) | 30.8 | 109 |
| Administration group (1 mg/kg) | 14.2 | 200 |
| Administration group (0.1 mg/kg) | 7.8 | 195 |
| Control group | 4.6 | 206 |

As seen from Table 4, plasmin activities in blood were remarkably increased in the administration groups and reached to, at highest, 7 times as high as that of the control group. The clot lysis time was decreased to a half of that of the control group, thus clearly showing the enhancement of plasmin activity.

EXAMPLE 11

Enhancement of Plasmin Activity by Intravenous Administration to Rabbits 2,3-Di-O-benzyl-5-O-phosphono-D-glucosaccharoascorbic acid n-octadecanethiolester sodium salt obtained by Example 2 was intravenously administered to rabbits. Blood was collected with time to prepare euglobulin fractions. The plasmin activities thereof were determined.

(1) Materials (a) Animals

Used animals were male rabbits (Japan White, body weight: 3.0–3.5 kg; Rabiton Farm).

(b) S-2251 solution

The same solution as prepared in Example 8 was used.

(2) Administration Method

A sample was suspended and dissolved in physiological saline at the concentration of 10 mg/5 ml. Then, the solution (1 mg/0.5 ml) was intravenously administered to rabbits anesthentized with urethane and sodium pentobarbital (0.5 mg/kg and 90 mg/kg, respectively, intraperitoneal administration), while the remaining 9 mg/4.5 ml was injected over 1 hour by sustained intravenous injection.

(3) Determination of Plasmin Activity

Plasmin activity was determined by the same manner as in Example 8.

According to the above method, the compound obtained in Example 2 was administered intravenously to rabbits (dosage: 3 mg/kg, 3 rats/group). Blood was collected 10, 30, 60, 90 and 120 minutes after the administration of the bolus to determine the plasmin activity in blood. Table 5 shows the average values of the results.

TABLE 5

| Blood collection time (min) | Plasmin activity in blood ($\Delta A405 \times 10^3$/min) | |
|---|---|---|
| | Administration group | Control group |
| 10 | 9.8 | 3.2 |
| 30 | 8.9 | 2.3 |
| 60 | 7.4 | 4.7 |
| 90 | 8.8 | 2.1 |
| 120 | 6.4 | 3.4 |

As seen from Table 5, plasmin activities in blood of the administration group were increased with increase in the doses and reached to 1.6 to 4.2 times as high as those of the control group.

What is claimed is:

1. A compound of the formula (I):

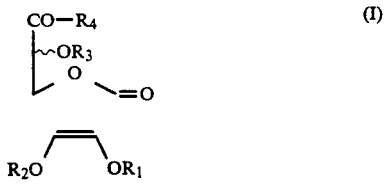

wherein $R_1$ and $R_2$ each is (1) a straight, branched or cyclic $C_{1-24}$ alkyl roup which is unsubstituted or is substituted by halogen, carboxyl or its ester, carbamoyl, nitro, cyano or $C_{1-4}$ alkoxy, provided that the cycloalkyl group may be additionally substituted by a $C_{1-4}$ alkyl group, or (2) a phenyl $C_{1-4}$ alkyl group which is unsubstituted or is substituted by halogen, carboxyl or its ester, carbamoyl, phenyl, nitro, cyano, $C_{1-4}$ alkoxy or $C_{1-4}$ alkyl optionally substituted by halogen; $R_3$ is a sulfo group or phosphono group; $—CO—R_4$ is an esterified carboxyl group, a thiol-esterified carboxyl group or an amidated carboxyl group; and $\sim$ represents the absolute configuration of R or S, or a pharmaceutically acceptable salt thereof.

2. A compound of claim 1 in which $R_1$ and $R_2$ are, the same or different and represent a phenyl-$C_{1-4}$ alkyl group or a straight or branched chain or cyclic $C_{1-24}$ alkyl group.

3. A compound of claim 1 in which both of $R_1$ and $R_2$ are benzyl.

4. A compound of claim 1 in which the esterified carboxyl group $—CO—R_4$ is a group represented by $—CO—O—R_5$ and the thiol-esterified group $—CO—R_4$ is a group represented by $—CO—S—R_6$ wherein $R_5$ and $R_6$ is a hydrocarbon residue having 1 to 24 carbon atoms.

5. A compound of claim 1 in which the amidated group $—CO—R_4$ is a group represented by

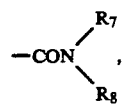

wherein $R_7$ and $R_8$ are a hydrogen atom or a hydrocarbon residue having 1 to 24 carbon atoms.

6. A comopund of claim 4 or 5 in which the hydrocarbon residue is a straight or branched chain or cyclic $C_{1-24}$ alkyl group, a phenyl-$C_{1-4}$ alkyl group or a phenyl group.

7. A compound of claim 1 in which $R_3$ is a phosphono group.

8. A comopund of claim 1 in which $—CO—R_4$ is a thiol-esterified carboxyl group.

9. A compound of claim 1 in which the absolute configuration represented by $\sim$ is S.

10. A compound of claim 1 which is 2,3-di-O-benzyl-5-O-sulfo-D-glucosaccharoascorbic acid n-octadecanthiolester, 2,3-di-O-benzyl-5-O-phosphono-D-glucosaccharoascorbic acid n-octadecanthiolester or 2,3-di-O-benzyl-5-O-phosphono-L-gulosaccharoascorbic acid n-octadecanthiolester or sodium salt thereof.

11. A compound of claim 1 which is 2,3-di-O-benzyl-5-O-phosphono-D-glucosaccharoascorbic acid n-octadecanthiolester sodium salt.

12. A pharmaceutical composition for preventing or treating thrombosis which comprises an effective amount of a compound of the formula (I) as defined in claim 1 or its pharmaceutically acceptable salt and a pharmaceutically acceptable carrier or excipient.

13. A pharmaceutical composition of claim 12 in which the compound of the formula (I) is a compound of any one of claims 2 to 8.

14. A method for preventing or treating thrombosis which comprises administering an effective amount of a compound of the formula (I) as defined in claim 1 or its pharmaceutically acceptable salt, optionally together with a pharmaceutically acceptable carrier or excipient to a human being suffering from thrombosis.

* * * * *

UNITED STATES PATENT AND TRADEMARK OFFICE
CERTIFICATE OF CORRECTION

PATENT NO. : 5,189,057

DATED : February 23, 1993

INVENTOR(S) : KOICHI KATO, HIROTOMO MASUYA and NORIHIKO MORIYA

It is certified that error appears in the above-identified patent and that said Letters Patent is hereby corrected as shown below:

On the cover page of the patent, in the Abstract, correct the formula to read:

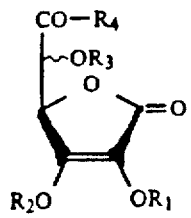

Column 2, line 20, correct the formula to read:

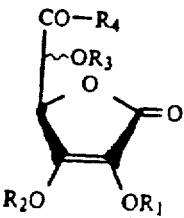

Column 17, line 30, correct the formula to read:

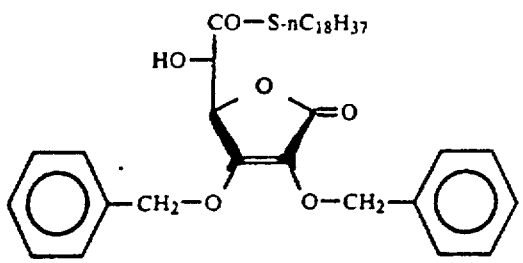

UNITED STATES PATENT AND TRADEMARK OFFICE
CERTIFICATE OF CORRECTION

PATENT NO. : 5,189,057
DATED : February 23, 1993
INVENTOR(S) : Koichi Kato, Hirotomo Masuya and Norihiko Moriya It is certified that error appears in the above-identified patent and that said Letters Patent is hereby corrected as shown below:

Column 18, line 5, correct the formula to read:

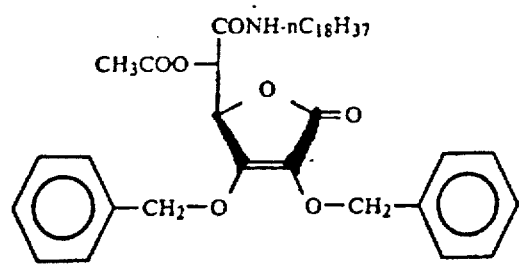

Column 18, line 45, correct the formula to read:

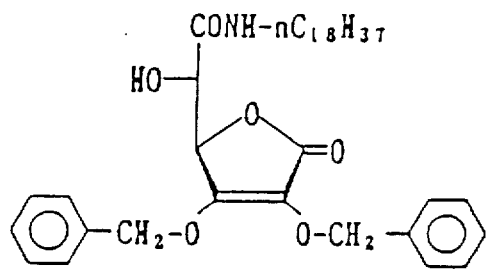

UNITED STATES PATENT AND TRADEMARK OFFICE
CERTIFICATE OF CORRECTION

PATENT NO. : 5,189,057

DATED : February 23, 1993

INVENTOR(S) : Koichi Kato, Hirotomo Masuya and Norihiko Moriya

It is certified that error appears in the above-identified patent and that said Letters Patent is hereby corrected as shown below:

Column 19, line 20, correct the formula to read:

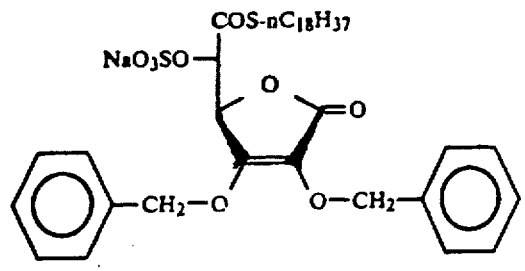

Column 19, line 60, correct the formula to read:

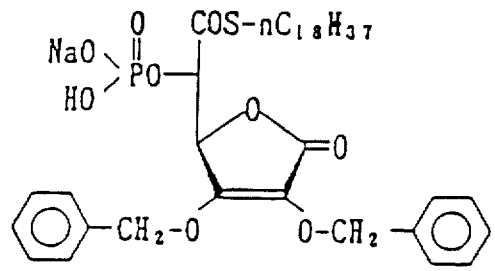

UNITED STATES PATENT AND TRADEMARK OFFICE
CERTIFICATE OF CORRECTION

PATENT NO. : 5,189,057

DATED : February 23, 1993

INVENTOR(S) : KOICHI KATO, HIROTOMO MASUYA and NORIHIKO MORIYA

It is certified that error appears in the above-identified patent and that said Letters Patent is hereby corrected as shown below:

Column 27, line 35, correct the formula to read:

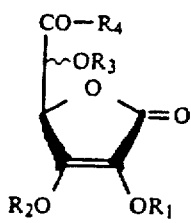

Signed and Sealed this

Twenty-second Day of March, 1994

*Attest:*

BRUCE LEHMAN

*Attesting Officer*  *Commissioner of Patents and Trademarks*